(12) United States Patent
Lichter

(10) Patent No.: US 6,676,961 B1
(45) Date of Patent: Jan. 13, 2004

(54) TRANSDERMAL PATCH ASSEMBLY

(75) Inventor: Richard R. Lichter, Waukesha, WI (US)

(73) Assignee: Automated Carrier Technologies, Inc., Waukesha, WI (US)

( * ) Notice: Subject to any disclaimer, the term of this patent is extended or adjusted under 35 U.S.C. 154(b) by 0 days.

(21) Appl. No.: 10/092,234

(22) Filed: Mar. 6, 2002

(51) Int. Cl.[7] ................................................ A61K 9/00
(52) U.S. Cl. ...................... 424/448; 424/448; 424/449
(58) Field of Search ................................ 424/448, 449

(56) References Cited

U.S. PATENT DOCUMENTS

| | | | |
|---|---|---|---|
| 2,235,436 A | 3/1941 | Laub | |
| 2,561,071 A | 7/1951 | Prisk | |
| 4,627,429 A | 12/1986 | Tsuk | |
| 4,695,277 A | 9/1987 | Lauk | |
| 4,784,857 A | 11/1988 | Berry et al. | |
| 4,821,733 A | * 4/1989 | Peck | 128/636 |
| 5,008,110 A | * 4/1991 | Benecke et al. | 424/448 |
| 5,098,421 A | 3/1992 | Zook | |
| 5,662,925 A | 9/1997 | Ebert et al. | |
| 5,788,983 A | 8/1998 | Chien et al. | |
| 5,820,876 A | 10/1998 | Hoffmann | |
| 6,113,940 A | 9/2000 | Brooke et al. | |
| 6,126,963 A | 10/2000 | Hoffmann | |
| 6,139,868 A | 10/2000 | Hoffmann | |
| 6,153,215 A | 11/2000 | Samuelsen et al. | |
| 6,214,374 B1 | 4/2001 | Schmirler et al. | |
| 6,264,976 B1 | 7/2001 | Heinecke et al. | |

* cited by examiner

Primary Examiner—Gollamudi S. Kishore
Assistant Examiner—Micah-Paul Young
(74) Attorney, Agent, or Firm—Andrus, Sceales, Starke & Sawall, LLP

(57) ABSTRACT

A transdermal patch assembly includes a pressure sensitive carrier having a central opening, one side being provided with a clear liner thereon extending across the central opening, and an opposite side being provided with a first adhesive coating thereon, the carrier having a thickness such that when combined with the clear liner, a cell is defined by walls of the central opening and an inwardly facing surface of the clear liner, the cell holding a pharmaceutical composition therein. The transdermal patch also includes a pharmaceutical diffusing cover having an overlying side with an outer periphery attached by the first adhesive coating to an inner periphery of the carrier opposite side, and an underlying side having a pair of opposed portions attached to a peelable release liner removably secured to an outer periphery of the carrier opposite side by the first adhesive coating.

14 Claims, 3 Drawing Sheets

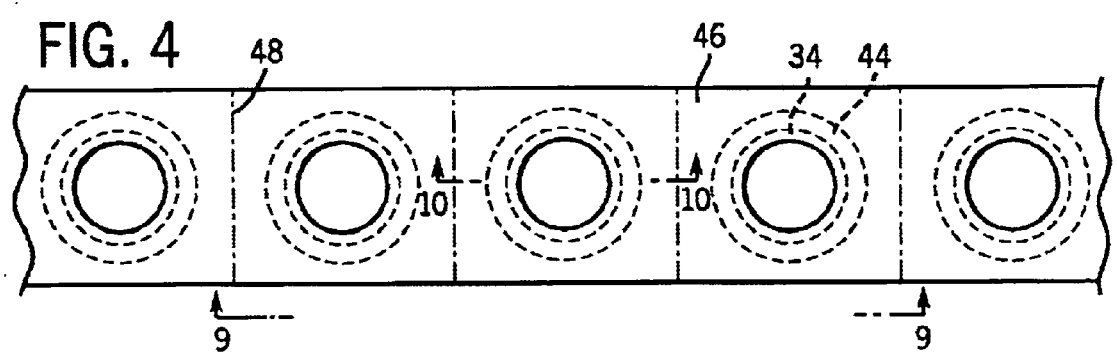
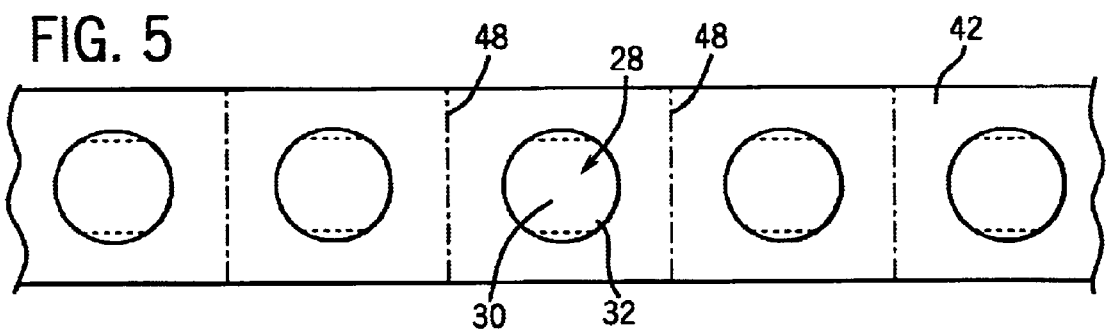
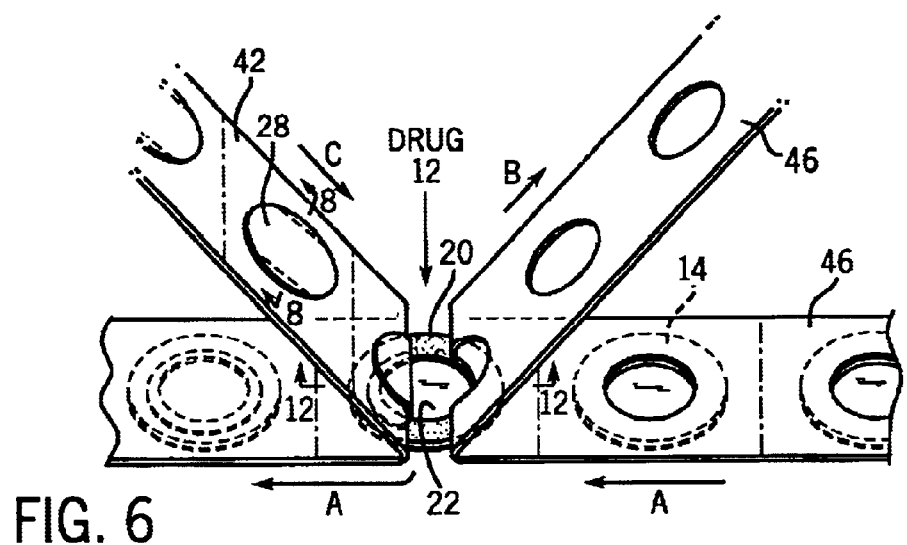
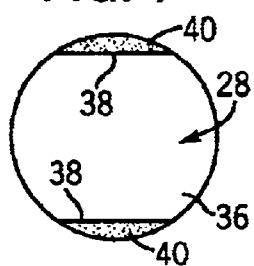
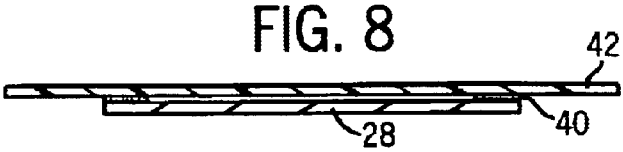

TRANSDERMAL PATCH ASSEMBLY

FIELD OF THE INVENTION

The present invention relates broadly to transdermal administration of pharmaceutical compositions and, more particularly, pertains to a patch assembly and method for producing same which are highly effective and are capable of wide spread use for small customized dose formulations as well as for large volume dose formulations.

BACKGROUND OF THE INVENTION

Much of the current research in drug delivery technology is aimed at developing formulations and devices that improve the therapeutic effectiveness of drugs over conventional means of administration by controlling the rate, time and place of release of drugs in the body. Conventional doses types include sublingual (under the tongue), oral (capsules, tablets, liquids), injectible, nasal and parenteral (suppository and non-oral) forms. While oral dosage forms comprise a substantial majority of all present dosage forms and offer ease of administration and low cost per use, they can suffer from inconvenient dosing intervals, side effects and reduced efficacy. Conventional dosage forms have disadvantages in certain patients including unpredictable blood levels, difficult or uncomfortable administration and poor compliance.

Controlled drug delivery systems have been introduced within the last decade to eliminate or reduce the limitations of conventional dosage forms. One type of controlled delivery is transdermal delivery, which involves delivery of a therapeutic agent through the skin for distribution within the body by circulation of the blood. Transdermal delivery can be compared to continuous, controlled intravenous delivery of a drug using the skin as a port of entry instead of an intravenous needle. The therapeutic agent passes through the outer layers of the skin, diffuses into the capillaries or tiny blood vessels in the skin and then is transported into the main circulatory system.

Transdermal patch devices which provide a controlled, continuous administration of a therapeutic agent through the skin are known as the art. Such devices, for example, are disclosed in U.S. Pat. Nos. 4,627,429; 4,784,857; 5,662,925; 5,788,983; and 6,113,940. Characteristically, these devices contain a therapeutic agent impermeable barrier layer which defines the outer surface of the device and a permeable skin attaching membrane, such as an adhesive layer, sealed to the barrier layer in such a way as to create a reservoir between them in which the therapeutic agent is placed. Although such devices may be satisfactory for their intended purpose, they have been found to be irritating to the wearer of the patch, provide minimized control of drug delivery through the skin, are slower to prepare, do not allow for customized formulation, are not easily produced and are not cost-effective.

Accordingly, there remains the need for a differently styled transdermal patch assembly which overcomes the drawbacks of the prior art and which is more easily and efficiently produced to address the individual needs of patients while also permitting high volume use.

SUMMARY OF THE INVENTION

In one aspect of the invention, a transdermal patch assembly includes a pressure sensitive carrier having a central opening, one side being provided with a clear liner thereon extending across the central opening, and an opposite side being provided with a first adhesive coating thereon, the carrier having a thickness such that when combined with the clear liner, a cell is defined by the walls of the central opening and an inwardly facing surface of the clear liner, the cell holding a pharmaceutical composition therein. The patch assembly also includes a pharmaceutical diffusing cover having an overlying side with an outer periphery attached by the first adhesive coating to an inner periphery of the carrier opposite side. The cover has an underlying side having a pair of opposed peripheral portions attached to a peelable release liner removably secured to an outer periphery of the carrier opposite side by the first adhesive coating. The carrier is preferably a foam substance while the clear liner is preferably a plastic material. Both the foam substance and the plastic material are impervious to the pharmaceutical composition. The pharmaceutical composition is comprised of a gel carrier and a drug. One side of the carrier is provided with a second adhesive coating for holding the clear liner in position. The cover is preferably comprised of tissue paper. The peripheral portions of the cover are generally semi-circular in shape and are provided with a third adhesive coating for attachment to the release liner. The release liner is impervious to the pharmaceutical composition. The release liner is preferably constructed of a clear plastic material. The release liner has an inner periphery which extends beyond the outer periphery of the carrier. The clear liner covers the entire one side of the carrier.

The invention further contemplates a method of assembling a transdermal patch comprising the steps of: a) providing at least one pressure sensitive carrier having a central opening, one side being provided with a clear liner thereon extending across the central opening, and an opposite side provided with a first adhesive coating thereon for removably holding a production liner thereon, the carrier including a cell defined by the walls of the central opening and an inwardly facing surface of the clear liner; b) providing at least one pharmaceutical diffusing cover having an overlying side with an outer periphery adapted to engage an inner periphery of the carrier when the production liner is removed from the carrier opposite side, and an underlying side having a pair of opposed peripheral portions removably attached to a peelable release liner adapted to removably engage an outer periphery of the carrier opposite side: c) removing the production liner from the carrier opposite side; d) depositing a pharmaceutical composition in the cell of the carrier; and e) affixing the outer periphery of the cover to the inner periphery of the carrier, and the peelable release liner to the outer periphery of the carrier. The step of providing at least one pressure sensitive carrier includes providing a perforated strip with a series of carriers. The step of providing at least one pharmaceutical diffusing cover includes providing a perforated strip with a series of covers. The method further contemplates a simultaneous operation of removing the production liner from the carrier opposite side, depositing a pharmaceutical composition in the cell of the carrier and affixing the outer periphery of the cover to the inner periphery of the carrier, and the peelable release liner to the outer periphery of the carrier.

Various other objects, features and advantages of the invention will be made apparent from the following description taken together with the drawings.

BRIEF DESCRIPTION OF THE DRAWINGS

The drawings illustrate the best mode presently contemplated of carrying out the invention.

In the drawings:

FIG. 4 is a plan view of a series of foam patches attached to a perforated production liner prior to assembly;

FIG. 5 is a plan view of a series of tissue covers attached to a perforated release liner prior to assembly;

FIG. 6 is partial perspective view of the assembly of the foam patches and the tissue covers after a drug is interposed between them;

FIG. 7 is a plan view of one side of the tissue cover which is attached to its release liner by semi-circular adhesive areas;

FIG. 8 is a sectional view taken on line 8—8 of FIG. 6;

DETAILED DESCRIPTION OF THE INVENTION

Figure 1:
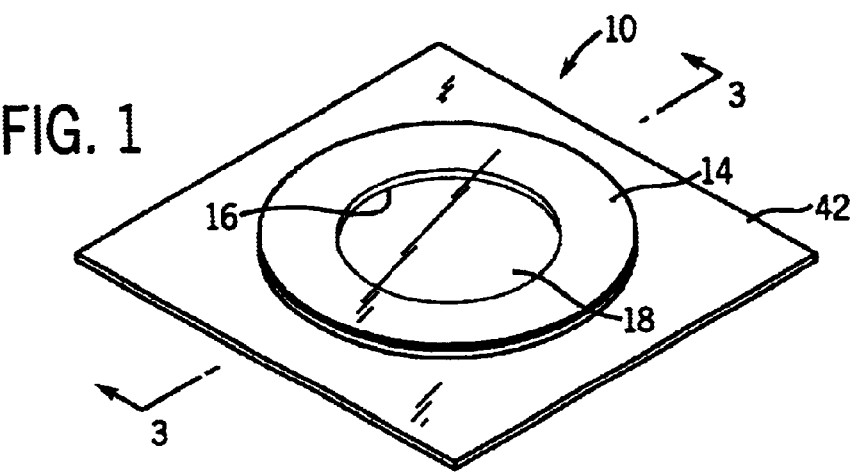
FIG. 1 is a perspective view of a transdermal patch assembly embodying the present invention.
Figure 2:
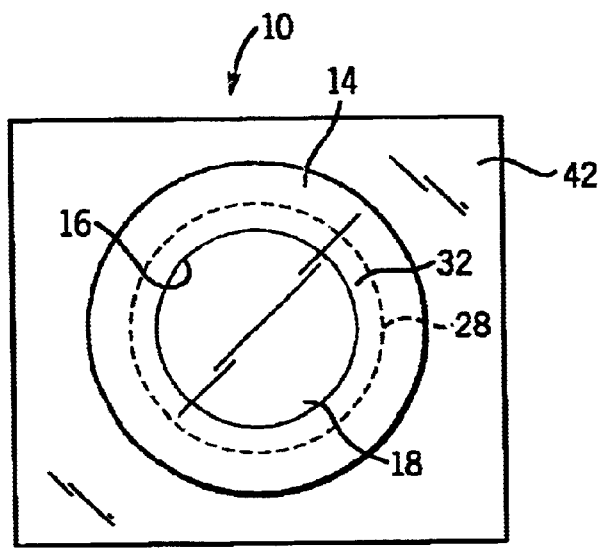
FIG. 2 is a plan view of the transdermal patch assembly of FIG. 1.
Figure 3:
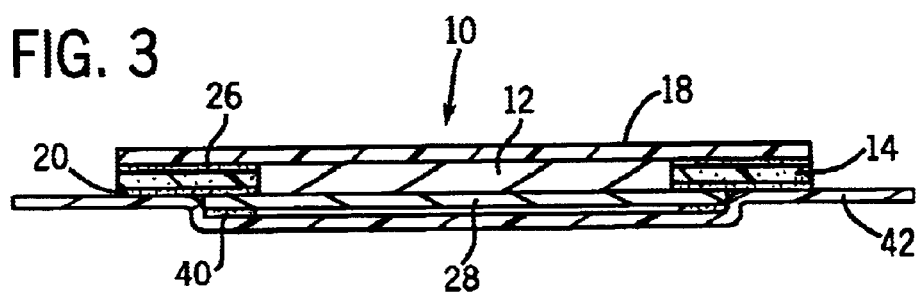
FIG. 3 is a sectional view taken on line 3—3 of FIG. 1.
Figure 9:
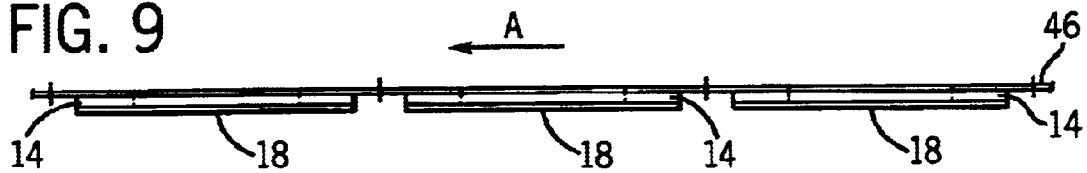
FIG. 9 is a sectional view taken on line 9—9 of FIG. 4.
Figure 10:
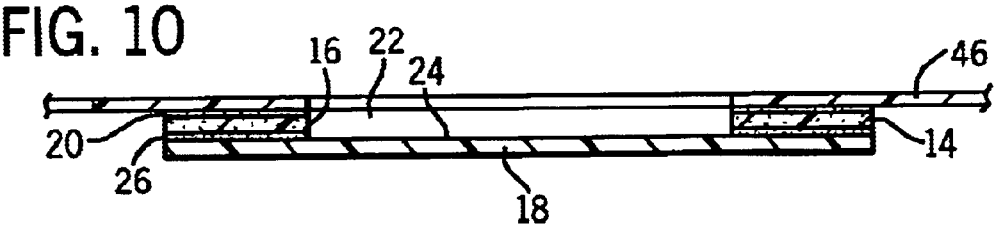
FIG. 10 is a sectional view taken on line 10—10 of FIG. 4.

Referring now to the drawings, FIGS. 1 through 3 illustrate a transdermal patch assembly 10 embodying the present invention that is designed to administer a pharmaceutical composition 12 to the skin. The patch assembly 10 is a laminated composite and includes a pressure sensitive carrier 14 having a central opening 16 with one side being entirely covered by a clear liner 18 extending across the central opening 16, and an opposite side being provided with a first adhesive coating 20 thereon. The carrier 14 is preferably fabricated from a foam material such as manufactured by Emtech Emulsion Technologies of Medina, Ohio. Such foam material is impervious to the pharmaceutical composition 12 and has a thickness such that when combined with the clear liner 18, a cell 22 (FIG. 10) is defined by the walls of the central opening 16 and an inwardly facing surface 24 of the clear liner 18. The clear liner 18 is typically made of a plastic material which is impervious to the pharmaceutical composition 12. The one side of carrier 14 is provided with a second adhesive coating 26 which is used to retain the clear liner 18 in position.

A cell 22 defines a repository for the pharmaceutical composition 12. In the preferred embodiment, the pharmaceutical composition 12 is comprised of a gel carrier, such as a hydrogel and a permeation enhancer, and a drug in the form of a hormone such as progesterone, estrogen, testosterone or a combination thereof. Such pharmaceutical composition is disclosed in U.S. Pat. No. 6,214,374 issued Apr. 10, 2001, which is incorporated by reference herein. It should be understood, however, that the pharmaceutical composition may include various other drugs such as contraceptives, analgesics, anti-inflammatories, bronchodilators, diuretics, anti-histamines, tranquilizers, anti-fungals, vitamins, muscle relaxants, and anti-virals.

The transdermal patch assembly 10 also includes a pharmaceutically diffusing tissue cover 28 having an overlying side 30 and an outer periphery 32 attached by the first adhesive coating 20 to an inner periphery 34 of the carrier opposite side. The cover 28 further has an underlying side 36 having a pair of semi-circular shaped, peripheral portions 38 (FIG. 7) removably fastened by a third adhesive coating 40 to a peelable release liner 42. The release liner 42, in turn, is detachably secured to an outer periphery 44 of the carrier opposite side by the first adhesive coating 20. The release liner 42 is preferably constructed of a clear plastic material which is impervious to the pharmaceutical composition 12.

In use, one simply peels away the release liner 42 which conveniently extends beyond the outer periphery of the carrier 14, and presses down on the outer periphery of the carrier 14 to affix the assembly 10 to the skin via the first adhesive coating 20. The pharmaceutical composition 12 will then begin to diffuse into the skin through the tissue cover 28. It should be understood that the size of the adhesively coated semi-circular portions 38 is minimized so that when the release liner 42 is peeled away, the delicate tissue cover 28 is not ripped or destroyed.

The clear liner 18 overlying the cell 22 allows the wearer of the patch assembly 10 to view the pharmaceutical composition 12 and be aware of its absorption through the skin. The gelatinous pharmaceutical composition 12 may "dry down" through evaporation if the patch assembly 10 is not used by the date code provided on the prescription for the patch assembly 10. As a feature of the invention, one can identify an expired patch assembly 10 by the translucent to opaque color of the tissue cover 28 becomes on expiration.

Figure 11:
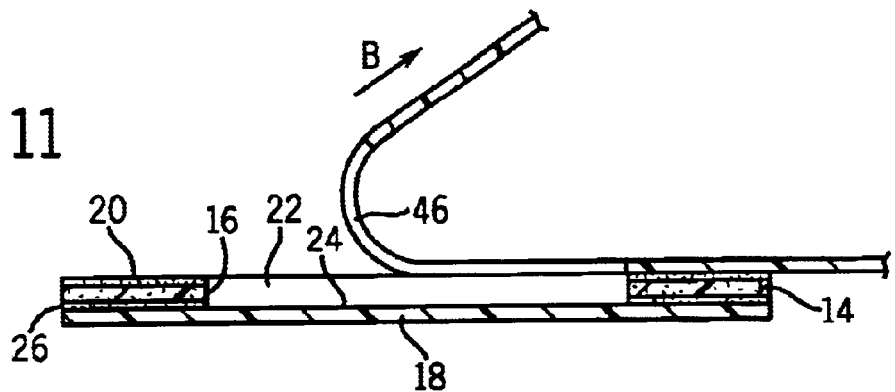
FIG. 11 is a sectional view showing the removal of the production liner from the foam patch.

Referring now to FIGS. 4 through 12, the invention also embraces a unique method of assembling the patch 10. As seen in FIGS. 4, 9, 10 and 11, at least one carrier 14 and preferably a series of carriers 14 is removably attached to a perforated production liner strip 46 by the first adhesive coating 20. Each carrier 14 is affixed to its clear liner 18 so as to define the cell 22 which will hold its particular pharmaceutical composition (drug) 12. The strip 46 is intended to move along in a production line fashion in the direction of arrow A in FIG. 9. FIG. 11 shows the particular manner in which each production liner segment is removed from its individual carrier 14 and attached clear liner 18 to expose the individual cell 22.

As seen in FIG. 5, at least one cover 28 and preferably a series of covers 28 is carried on a perforated release liner 42. Each cover 28 has its underlying side 36 provided with opposed semi-circular, peripheral portions 38 (FIG. 7) carrying the third adhesive coating 40 used to lightly and removably fasten the cover 28 to its release liner 42 as depicted in FIG. 8. The overlying side 30 of each cover 28 has outer periphery 32 adapted to be affixed to the carrier 14 as will be detailed below.

Figure 12:
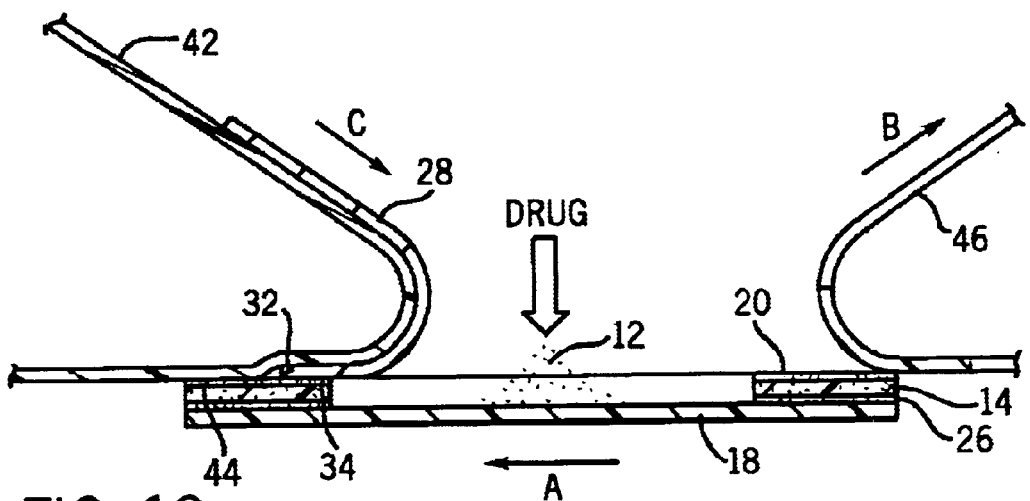
FIG. 12 is a sectional view representing the assembly shown in FIG. 6.

Turning now to FIGS. 6 and 12, as the carriers 14 are moved along a surface in the direction of arrow A, the production liner strip 46 is pulled back and away to the right in the direction of arrow B. This motion separates each carrier 14 so that its cell 22 is exposed and the carrier opposite side with the first adhesive coating 20 faces upwardly. As the strip 46 is being pulled back and away, the pharmaceutical composition (drug) 12 is deposited in the cell 22, the strip being pulled back at a rate which will protect the first adhesive coating 20 on the carrier 14 from drug spill or contamination. Substantially simultaneously as the drug 12 is being deposited in the cell 22, the release liner 42 is moved in the direction of arrow C. This places the outer periphery 32 of cover overlying side 30 into engagement with the first adhesive coating 20 on the inner periphery 34 of the carrier 14, and also attaches the release liner 42 to the outer periphery of the carrier 14. Finished patch assemblies 10 continue to move in the direction of arrow A. Perforations 48 on the release liner 42 are used to separate individual patch assemblies 10 from one another.

It has been found that the patch assembly of the present invention is comfortable when placed on the skin, and provides better control of drug delivery through the skin. It has also been realized that the patch assembly is more quickly and cost effectively prepared as it does not require multiple laminations or heat sealing. The patch assembly may be used to provide custom dose formulations (such as single prescriptions) which may be easily prepared while a customer waits such as at a neighborhood pharmacy. The patch assembly may also be utilized in medium volume formulation for consumer use where several hundred thousand and up to 50 million patches may be required yearly. The patch assembly makes it possible to transdermally deliver a wide range of drugs including vitamins and other nutrients. It should be appreciated that ease of use is one of the major benefits of the patch assembly and that anyone can produce the patch assembly with minimal instructions.

While the invention has been described with reference to a preferred embodiment, those skilled in the art will appreciate that certain substitutions, alterations and omissions may be made without departing from the spirit thereof. Accordingly, the foregoing description is meant to be exemplary only, and should not be deemed limitative on the scope of the invention set forth with the following claims.

I claim:

1. A non-heat-sealed transdermal patch assembly consisting essentially of:
    a stationary pressure sensitive carrier having a central opening, one side being provided with a stationary clear liner thereon extending across the central opening, and an opposite side being provided with a first adhesive coating thereon, the carrier having a thickness such that when combined with the clear liner, a cell is defined by walls of the central opening and an inwardly facing surface of the clear liner, the cell holding a pharmaceutical composition therein; and
    a pharmaceutical diffusing tissue paper cover having an overlying side with an outer periphery attached by the first adhesive coating to an inner periphery of the carrier opposite side, and an underlying side having only a pair of opposed peripheral portions attached to a peelable release liner removably secured to an outer periphery of the carrier opposite side by the first adhesive coating.

2. The transdermal patch assembly of claim 1, wherein the carrier is a foam material impervious to the pharmaceutical composition.

3. The transdermal patch assembly of claim 1, wherein the clear liner is a plastic material impervious to the pharmaceutical composition.

4. The transdermal patch assembly of claim 1, wherein the pharmaceutical composition is comprised of a gel carrier and the drug.

5. The transdermal patch assembly of claim 1, wherein the one side of the carrier is provided with a second adhesive coating for holding the clear liner in position.

6. The transdermal patch assembly of claim 1, wherein the peripheral portions are generally semi-circular in shape and are provided with a third adhesive coating for attachment to the release liner.

7. The transdermal patch assembly of claim 1, wherein the release liner is impervious to the pharmaceutical composition.

8. The transdermal patch assembly of claim 1, wherein the release liner is constructed of a clear plastic material.

9. The transdermal patch assembly of claim 1, wherein the release liner has an outer periphery which extends beyond the outer periphery of the carrier.

10. The transdernal patch assembly of claim 1, wherein the clear liner covers the entire one side of the carrier.

11. The method of assembling a non-heat-sealed transdermal patch, the method consisting essentially the steps of:
    a) providing at least one stationary pressure sensitive carrier having a central opening, one side being provided with a stationary clear liner thereon extending across the central opening, and an opposite side provided with a first adhesive coating thereon for removably holding a production liner thereon, the carrier including a cell defined by walls of the central opening and an inwardly facing surface of the clear liner;
    b) providing at least one pharmaceutical diffusing tissue paper cover having an overlying side with an outer periphery adapted to engage an inner periphery of the carrier when the production liner is removed from the carrier opposite side, and an underlying side having only a pair of opposed peripheral portions removably attached to a peelable release liner adapted to releasably engage an outer periphery of the carrier opposite side;
    c) removing the production liner from the carrier opposite side;
    d) depositing a pharmaceutical composition in the cell of the carrier; and
    e) affixing the outer periphery of the cover to the inner periphery of the carrier, and the peelable release liner to the outer periphery of the carrier.

12. The method of claim 11, wherein the step of providing at least one pressure sensitive carrier includes providing a perforated strip with a series of carriers.

13. The method of claim 12, wherein the step of providing at least one pharmaceutical diffusing cover includes providing a perforated strip with a series of covers.

14. The method of claim 11, wherein the steps c), d), and e) are performed simultaneously.

* * * * *